(12) United States Patent
Barnard et al.

(10) Patent No.: US 11,987,430 B2
(45) Date of Patent: May 21, 2024

(54) FOOD SPOILAGE MONITORING DEVICE

(71) Applicant: Mimica Lab Ltd, Newmarket (GB)

(72) Inventors: Joanne Barnard, London (GB); David Harpur, Ballinlough (IE); Giorgia Raci, Liverpool (GB); Iasmi Kalathaki, Manchester (GB); Lawrence Matthews, Dullingham (GB); Solveiga Pakstaite, London (GB)

(73) Assignee: Mimica Lab Ltd, Newmarket (GB)

( * ) Notice: Subject to any disclaimer, the term of this patent is extended or adjusted under 35 U.S.C. 154(b) by 253 days.

(21) Appl. No.: 17/762,841

(22) PCT Filed: Sep. 15, 2020

(86) PCT No.: PCT/EP2020/075762
§ 371 (c)(1),
(2) Date: Mar. 23, 2022

(87) PCT Pub. No.: WO2021/058335
PCT Pub. Date: Apr. 1, 2021

(65) Prior Publication Data
US 2022/0332482 A1     Oct. 20, 2022

(30) Foreign Application Priority Data
Sep. 26, 2019   (GB) .................................... 1913884

(51) Int. Cl.
*B65D 51/28*   (2006.01)
*B65D 41/34*   (2006.01)
(Continued)

(52) U.S. Cl.
CPC .............. *B65D 51/28* (2013.01); *B65D 41/34* (2013.01); *B65D 51/245* (2013.01); *G01N 33/02* (2013.01)

(58) Field of Classification Search
CPC ...... B65D 51/28; B65D 41/34; B65D 51/245; B65D 79/02; B65D 81/32; G01N 33/02; G01N 33/0001; G01N 33/14
(Continued)

(56) References Cited

U.S. PATENT DOCUMENTS 2,823,131 A   2/1958  Power
3,067,015 A   12/1962 Lawdermilt
(Continued)

FOREIGN PATENT DOCUMENTS

DE        19910962 A1    9/2000
WO     WO 2019029892 A1  2/2019

OTHER PUBLICATIONS

Solveiga Pakstaite, Apr. 24, 2019, Accurate food freshness indication with Mimica, YouTube [online].
(Continued)

*Primary Examiner* — Don M Anderson
*Assistant Examiner* — Eric C Baldrighi
(74) *Attorney, Agent, or Firm* — Hartman Titus PLC; Joseph W Mott

(57) ABSTRACT

An activatable spoilage monitoring device (2) is housed in a lid for a container. The device comprises a reservoir containing a digestor fluid and a tray (62) containing a digestible material or gel and having a tactile pattern of protuberances (68) formed in a base of the tray. The two parts (4, 6) of the lid axially compress together as the lid is opened resulting in activation of the device by permitting the fluid to come into contact with the digestible material.

15 Claims, 5 Drawing Sheets

(51) Int. Cl.
*B65D 51/24* (2006.01)
*G01N 33/02* (2006.01)

(58) Field of Classification Search
USPC .......................................................... 215/227
See application file for complete search history.

(56) References Cited

U.S. PATENT DOCUMENTS

| | | | |
|---|---|---|---|
| 4,003,709 A | 1/1977 | Eaton | |
| 5,265,744 A * | 11/1993 | Duty | B65D 50/041 |
| | | | 215/250 |
| 9,915,638 B2 | 3/2018 | Pakstaite | |
| 10,625,913 B2 * | 4/2020 | Acevedo | B65D 50/00 |
| 2002/0195413 A1 * | 12/2002 | Eastman | B65D 55/026 |
| | | | 215/230 |
| 2019/0154571 A1 | 5/2019 | Kuczynski et al. | |

OTHER PUBLICATIONS

Available from https://www.youtube.com/watch?v=4vZwiz2soW0 [Accessed Mar. 29, 2022] Screen image at 1:05.

* cited by examiner

SECTION A-A

US 11,987,430 B2

FOOD SPOILAGE MONITORING DEVICE

TECHNICAL FIELD

The present invention relates to the technical field of monitoring the shelf life of food products, particularly beverages and other bottled products.

PRIOR ART

An approach to food spoilage monitoring is described in U.S. Pat. No. 9,915,638 13 Mar. 2018 (PAKSTAITE) which provides a monitoring device in the form of a label that offers a tactile response indicating food spoilage when a layer of material above a bumpy or ridged surface has liquefied. Synchronising the phase transition of the material with the rate of spoilage of the packaged foodstuff allows a more efficient indication of food quality than the traditional best before date marking. This is because the label and the food product are subject to the same environmental conditions during transit and storage.

Technical Problems

However, some products will only start the decay or spoilage process after a package has been opened. In some products opening will accelerate the decay or spoilage process. Therefore, there is a technical problem in monitoring this, as it then becomes necessary to activate the label so that it replicates the same conditions as the product only after activation. There is therefore a technical problem in providing for activation on opening of a package.

When using a tactile sensing device, it is necessary for the device to be supported on the packaging such that it can be felt easily without interference from other responses generated by the packaging. There is therefore a technical problem in providing support for the device.

The present invention therefore addresses the above described technical problems.

SOLUTION OF THE PRESENT INVENTION

The present invention is defined in the appended claims.

Many beverages and food products are packaged in bottles which use a standard screw cap or lid closure and embodiments of the present invention are designed to be incorporated into such a lid. Preferably the device is activated using the same motion that is necessary to open the lid of the container. The device can be supported within the lid which typically already has a sufficiently rigid underlying surface. This facilitates reliability and the use of the tactile monitoring device.

DESCRIPTION OF THE DRAWINGS

In order that the invention can be well understood some embodiments thereof will now be described, by way of example only, with reference to the accompanying diagrammatic drawings, in which.

DESCRIPTION OF AN EMBODIMENT

Figure 3:
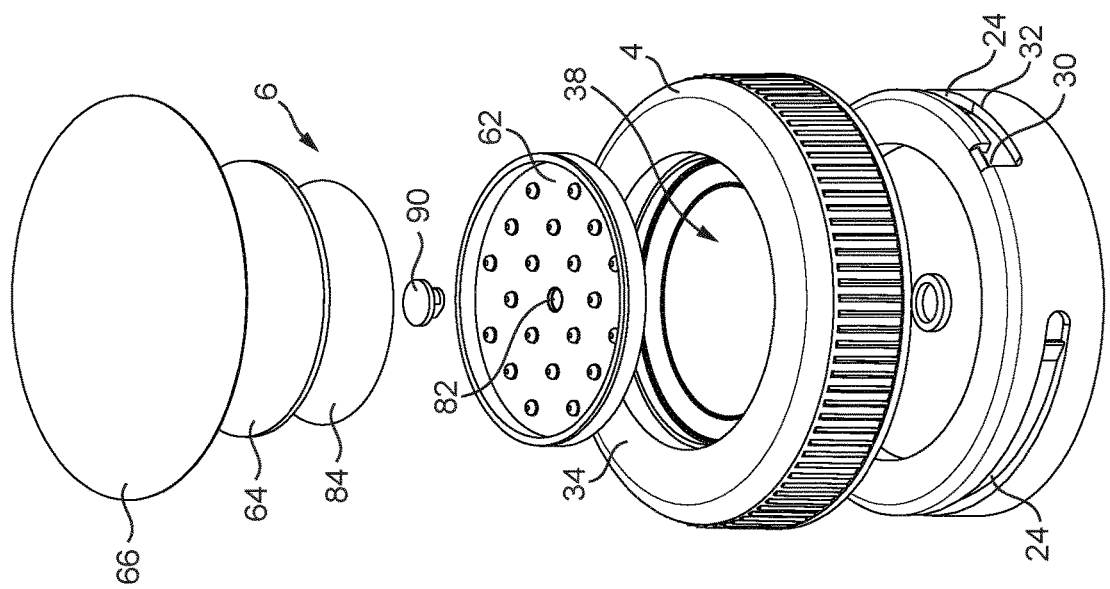
FIG. 3 is an exploded view showing the component parts of a lid incorporating the device of FIGS. 1 and 2.

An activatable food spoilage monitoring device 2 is mounted into an upper part 4 of a two-part cap or lid 6. The lid 6 may be of any standard size either for fitting to a glass or plastics bottle or jar or any other packaging container having a screw neck. A lower part 8 of the lid 6 has an annular wall component 12 having an internal screw thread 10 to engage in a conventional manner with a screw neck. The annular wall component is closed at its upper surface by a recessed top panel 14. The top panel 14 has a circular indentation 16 which engages with a correspondingly shaped circular projection 18 in the upper part. The profile in plan of the indentation and projection could take any appropriate shape provided they match and interlock and permit at least a limited relative rotation of the indentation and projection. As shown in this first embodiment, the indentation has a circular rib 20 which supports a lower wall of the projection 18 which contains the spoilage monitoring device 2. On the outer side of the wall component 12, oppositely disposed, elongate L-shaped grooves 24 are formed. This groove 24 is best shown in FIG. 3 where its shape can be appreciated. Each groove is designed to cooperate with an inwardly projecting peg 26 formed on an inner wall surface of the upper part of the lid. The groove has an entry section 30 which extends from an intermediate point in the wall to the top panel. The entry section merges with a downwardly sloped track 32 so that on rotation of the upper part relative to the lower part, the two parts compress together into the configuration shown in FIG. 2. It will be appreciated that more than two guidance grooves could be used for larger diameter lids. Alternative guidance systems that function in a similar manner can also be employed.

Figure 1:
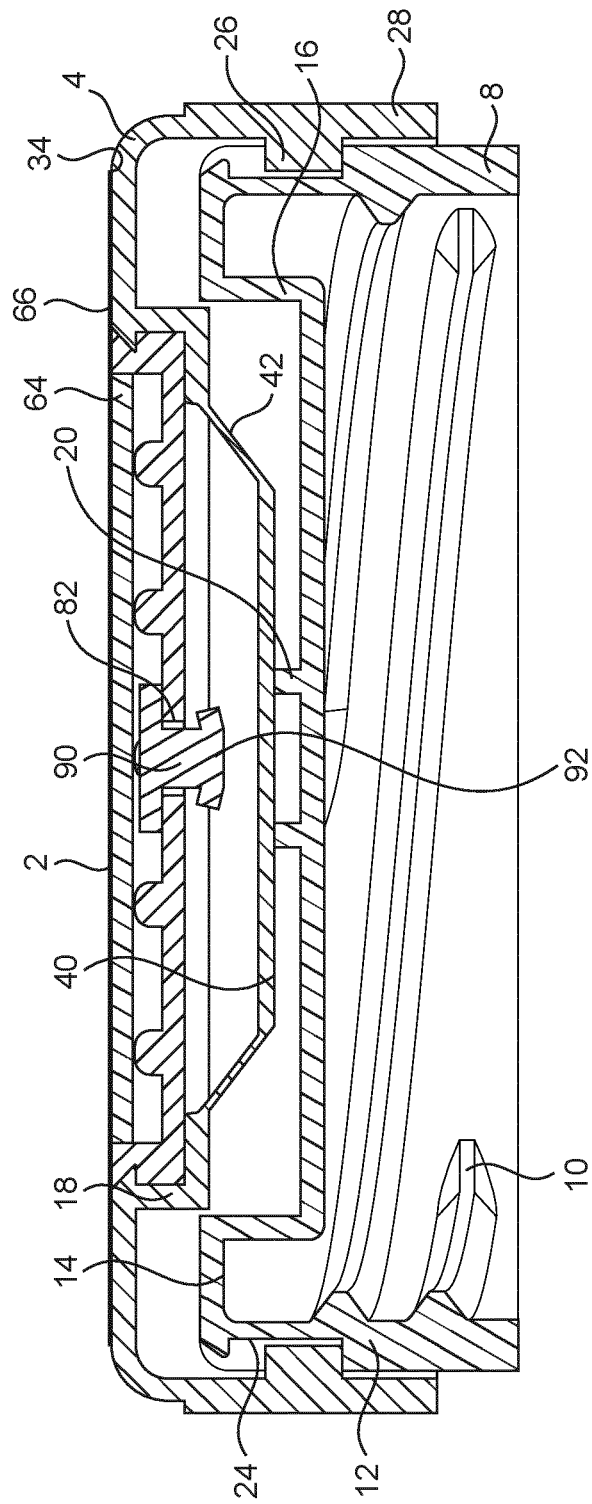
FIG. 1 shows a cross section through a lid incorporating an activatable spoilage monitoring device in accordance with a first embodiment of the invention in a pre-activated condition.

The upper part 4 of the lid 6 is a cup-shaped member having an annular wall 28 and a top panel 34. The top panel contains the circular shaped projection 18 which defines within it a recessed cavity 38 into which the monitoring device 2 can be received. The cavity has a base 40 which has a flexible central portion surrounded by a flexible, peripheral, downwardly-sloped annular wall section 42. As can be seen in FIG. 1, when the device is in a pre-activated condition, the central portion of the base 40 is supported on the rib 20 of the indentation 16 in the lower part. Due to the flexibility of the annular ring 42, the central portion 40 can be inverted or "popped up" in order to activate the device when the two lid parts are rotated relative to one another. In this first embodiment the annular ring 42 is made of a weakened thin material so that the base can be pushed flat against the bottom of the device 2.

Figure 2:
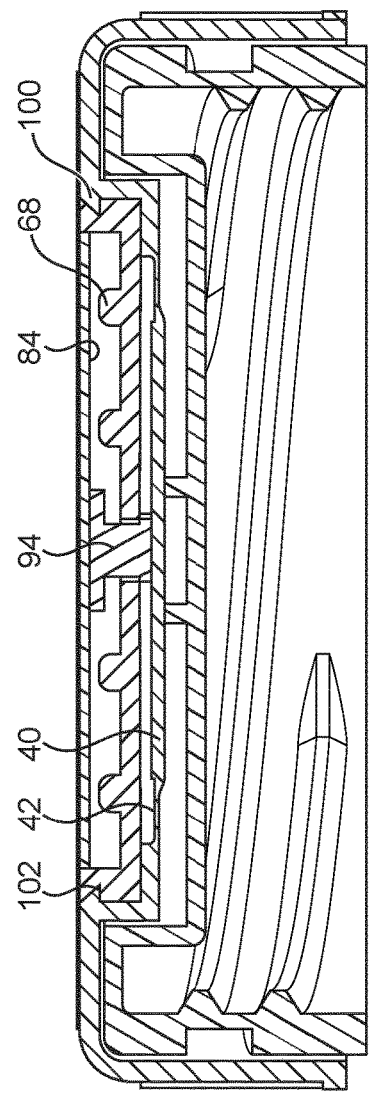
FIG. 2 is a cross section through the lid of FIG. 1 after activation.

The annular wall 28 is provided with two oppositely disposed pegs 26 which seat within the grooves 24 of the lower part. The pegs 26 are visible in FIG. 1. In FIG. 2, the upper part has been rotated relative to the lower part which forces the upper part downwardly into the configuration shown in FIG. 2. During this rotation the central portion of the base will be forced to pop up into the configuration shown in FIG. 2.

The cavity 38 receives the spoilage monitoring device 2. This device consists of a reservoir defined within the bottom of the cavity 38. This reservoir contains a digestor fluid or liquid. An insert tray 62 with a base provided with a tactile pattern of protuberances, such as a series of ridges or bumps or pimples 68 sits above the reservoir cavity. The tray receives a layer 64 of a digestible material, for example, gelatine, gel, hydrocolloid or hydrogel. The term gel will be used as a generic term for this material layer. The gel may contain other chemicals to moderate its decay process into a liquid. The choice of digestor liquid and digestible material is dependent on the contents of the product package within the container sealed by the lid. A flexible film 66 seals the device 2 within the cavity 38.

The base of the tray 62 has a central channel 82 which in the pre-activated condition is sealed by a dumbbell shaped rubber valve 90 which is push fitted into the channel prior to the introduction of the layer of digestible gel. The valve 90 has a portion 92 which is retained below the channel and a sealing portion 94 held above it. When the base 40 of the recess 38 comes into contact with a lower portion 92 of the valve, it pushes the upper sealing portion 94 away from the channel 82 opening the valve to allow digestor fluid to flow through the channel.

The gel layer 64 has a thin layer of material or cloth 84 at its lower surface. This cloth could be made of paper or sponge or any other absorptive material that is capable of absorbing the digestor liquid in order to disperse it when it enters the tray on activation.

It is necessary in this embodiment that the sides of the tray are to be fitted tightly to the upper part of the cap so that the digester liquid can only go through the valve seal channel. This tight fit can be achieved by the addition of a snap fit groove 100 around an upper external wall of the tray. An inwardly projecting nib 102 is provided around the upper circumference of the cavity in order to engage with the groove 100 to seal the device 2 into the cavity 38, in such a way that any digester liquid in the reservoir cannot escape.

In operation, when the lid is unscrewed in the normal way about an axis which is vertical in ordinary use, the first part of the rotation will cause the two parts of the lid to axially compress together reducing the spacing between the two parts. As a result, pressure on the lower portion of the valve from the base 40 results in the opening of the valve 90 allowing the digester liquid to be squeezed up and through the channel 82 onto the bottom of the tray under the gel. The valve 90 can be made of various different designs. It can be opened either mechanically by being pushed by the flexible base as described above or be opened by the increased pressure that is created underneath the tray when the flexible base is pushed up during activation. Once the digestor liquid is in the tray, the thin cloth 84 absorbs the liquid quickly in order to disperse the liquid over the entire bottom surface of the gel. The gel then absorbs the digester liquid from the cloth. The cloth ensures an even spread of the digester liquid over the surface of the gel and prevents the digester liquid from running back under the tray should the flexible base 40 be re-expanded Further rotation of the lid will open the container in the conventional manner so that the contents can be accessed and the container resealed by reapplication of the lid. The activation process cannot be reversed. The activation process by rotation of the parts is a one-way operation and results in the irreversible chemical activation by the digestor liquid entering the tray. It is desirable to be able to lock the activation state. This can be achieved by shaping the end of the groove 24 to capture the peg and prevent it moving backwards as shown in FIG. 3. Activation can also be insured by the interlocking created by the popping up process of the base 40. Other methods of achieving activation could be used. Irreversible mechanical activation may be desirable because reversal could allow the fluid to come out of contact with the gel to create unreliable results. In other arrangements where the absorption of the fluid into the gel is sufficient to ensure irreversible activation (that is the chemical reaction is permanent) the rotation mechanism can be made reversible, in order to neutralise the positive pressure in the cap resulting from the initial activation compression. This makes it easier to feel the bumps once liquefied, because it is less bulgy'. Accordingly the physical mechanism may be reversible; but the activation chemical reaction between the activator and the gel is irreversible.

As time passes, the digestor liquid is absorbed by the gel and begins the temperature dependent decay process which will eventually force the gel to liquefy. When the gel is liquefied, a user touching the film 66 will be able to feel the tactile pattern moulded into the base of the tray. When the gel is solid and the contents of the container are still fresh, the user will feel a smooth surface. Accordingly, the device 2 allows the user to detect when the decay process has proceeded sufficiently far for the gel to liquefy. By appropriate choice of gel and digestor liquid, the decay process in the gel can be made to mimic the anticipated freshness of the contents of the container.

The film 66 is sealed to the upper part of the lid. Ultrasonic welding can be used. Other methods of creating a seal over the sponge could be employed. The two parts of the lid can be injection moulded plastics. Other forms of fabrication such as vacuum casting could be used. The overall height of the lid can be made to match the overall height of a conventional lid so that this type of lid can be simply used in the packaging process in like for like replacement of conventional screw top lids or caps.

Figure 7:
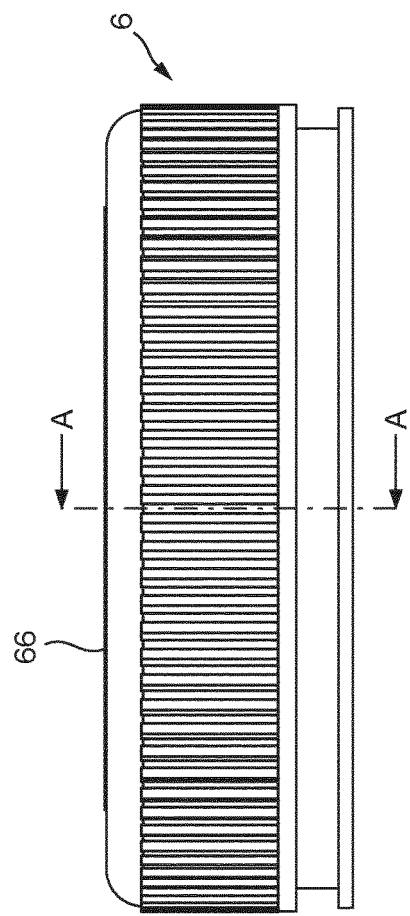
FIG. 7 is a side view of the lid of the first or second embodiment prior to activation.
Figure 8:
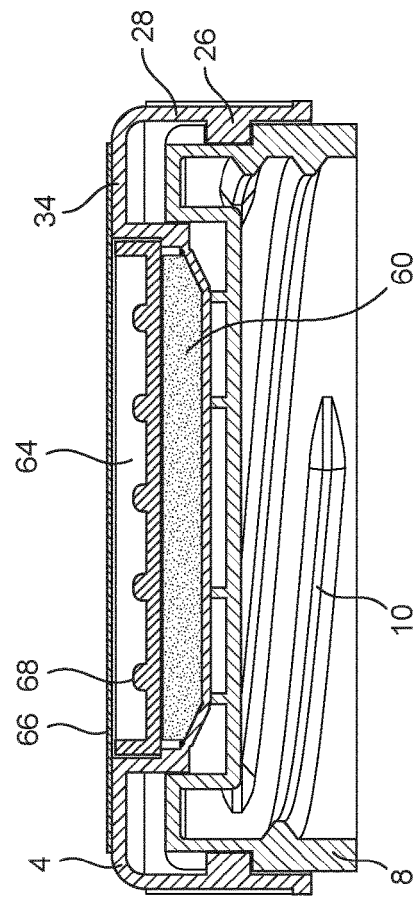
FIG. 8 is a cross section on line A-A in FIG. 7 at right angles to the section shown in FIGS. 4, showing the internal structure of the second embodiment of the invention and the locked relative position of the parts of the cap before activation.
Figure 6:
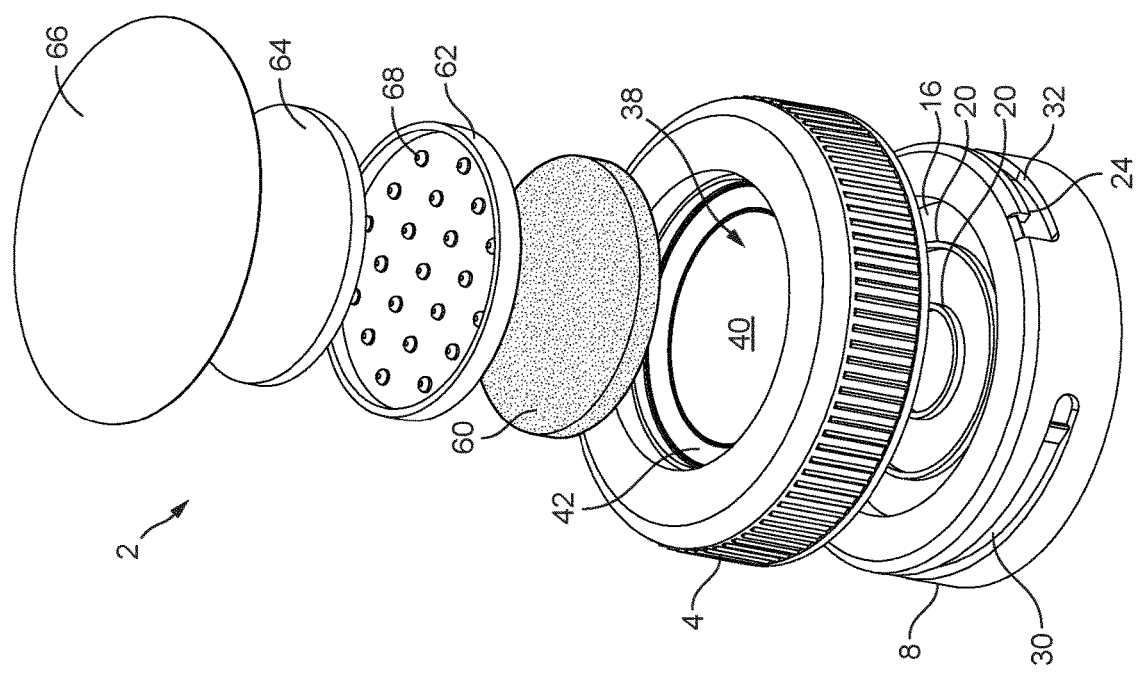
FIG. 6 is an exploded view showing the component parts of a lid incorporating the device of FIGS. 4 and 5.

Preferably the outer side of the wall of the upper part 4 is knurled as shown in FIG. 7 to facilitate gripping of the part to initiate rotation.

Second Embodiment

Figure 4:
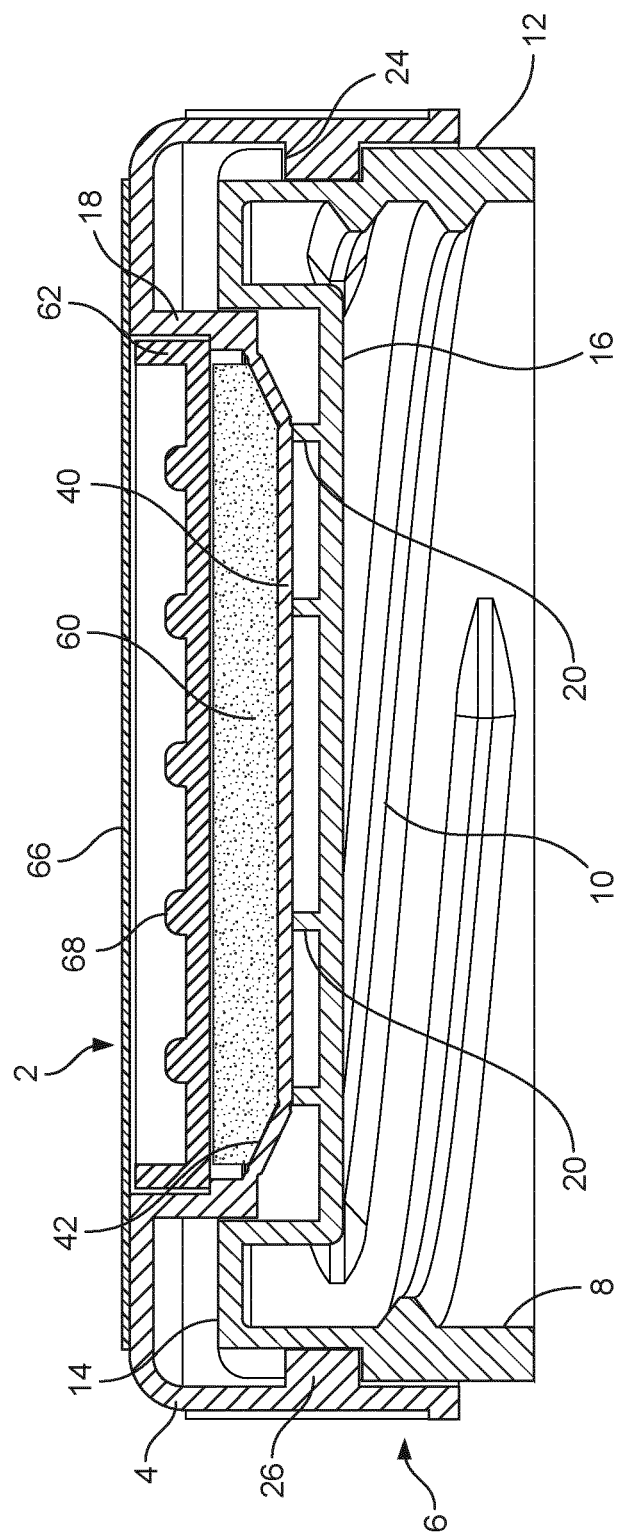
FIG. 4 shows a cross section through a lid incorporating an activatable spoilage monitoring device in accordance with a second embodiment the invention in a pre-activated condition.

The second embodiment is illustrated in FIGS. 4 to 8 and like parts are indicated by like reference numerals. The general principle of the second embodiment is as previously described. In this embodiment the digestor fluid is contained in a sponge 60 which fills the reservoir 38. The sponge may be made of cellulose or other suitably absorbent material. The type of material used needs to be able to store the required amount of digestor liquid and expel substantially all of it when compressed. As shown in FIG. 4, there are two concentric ribs 20 which support the base 40 of the reservoir in this embodiment in order to create greater force on the sponge 60.

Figure 5:
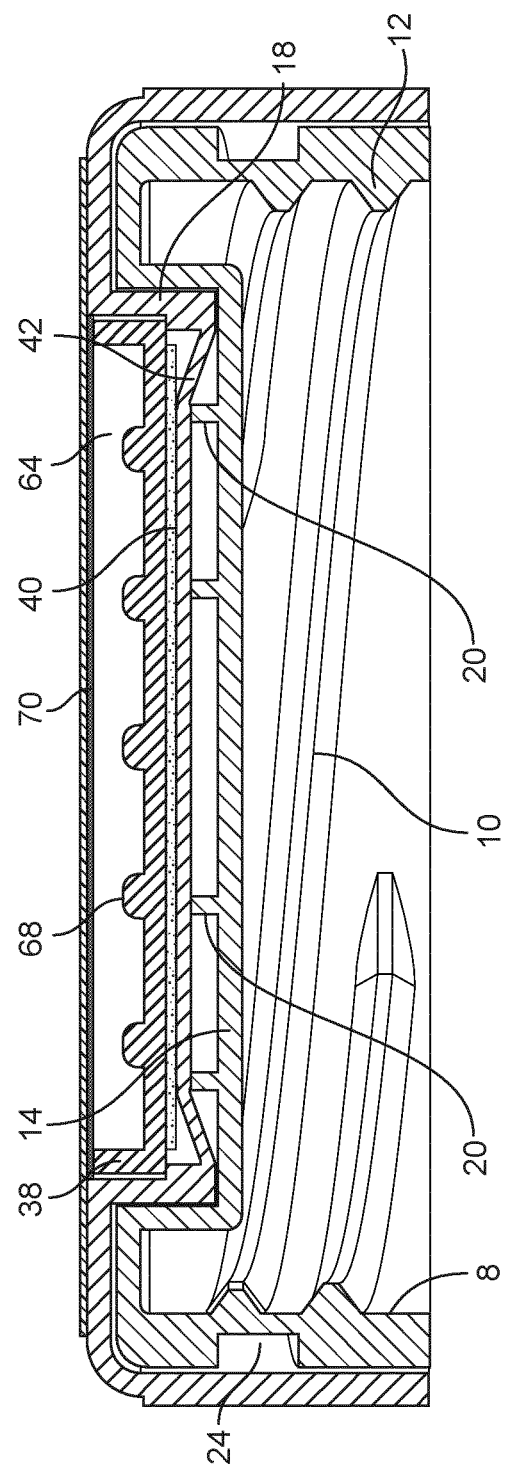
FIG. 5 is a cross section through the lid of FIG. 4 after activation.

On activation of the device the side wall of the reservoir is popped up into an inverted position as shown in FIG. 5 to apply uniform pressure to the sponge and cause the digestor fluid to flow around and over the edges of the tray and onto the gel 64. The inversion of the flexible base 40 squeezes the digestor liquid out of the sponge, around and over the sides of the tray and onto the top of the gel layer as diagrammatically illustrated in FIG. 5, where the digestor liquid is shown as a layer 70 sitting on top of the gel.

The tray 62 could also have perforations in its base to allow entry of the digestor fluid squeezed out of the sponge.

It will be appreciated that this embodiment with a sponge in the reservoir could be combined with the first embodiment, with the base of the tray provided with a valve sealed channel as in the first embodiment in order to deliver the digestor fluid into a cloth lined base of the tray on activation.

The method of operation of the second embodiment is as previously described.

The invention claimed is:

1. A lid for closing a container comprising
a first part having an indentation adapted to receive a projection of a second part, the projection defining a cavity into which a spoilage monitoring device is received;
the spoilage monitoring device comprising a reservoir containing a digestor fluid and a tray containing a digestible material, wherein the tray has a base with a raised tactile pattern formed thereon and the digestible material covers the base with a smooth surface, and the base of the tray defines a channel sealed by a valve that is opened on activation of the device; wherein an axial movement of the parts relative to each other causes irreversible activation of the device such that the digestor fluid is absorbed by the digestible material liquefying it over a period of time, whereupon the smooth surface is dissipated and a user is able to feel the raised tactile pattern.

2. A lid as claimed in claim 1 wherein the tray is sealed into the cavity to prevent escape of digestor fluid from the reservoir.

3. A lid as claimed in claim 2 wherein the tray is sealed by a snap fit between the projection and the device.

4. A lid as claimed in claim 1, wherein the two parts rotate relative to one another in order to axially reduce the spacing between them forcing the digestor fluid out of the reservoir.

5. A lid as claimed in claim 4 wherein the tray is sealed into the cavity to prevent escape of digestor fluid from the reservoir.

6. A lid as claimed in claim 5 wherein the tray is sealed by a snap fit between the projection and the device.

7. A lid as claimed in claim 1 wherein the reservoir contains a sponge.

8. A lid as claimed in claim 7, wherein a base of the projection is made of a flexible material having a central part for supporting the sponge, and a peripheral inclined wall section which in a pre-activated condition is downwardly sloping and in an activated condition is upwardly sloping to compress the sponge.

9. A lid as claimed in claim 1 wherein a thin layer of absorbent material is provided underneath the digestible material in order to distribute digestor fluid across the surface of the digestible material.

10. A lid as claimed in claim 7 wherein a thin layer of absorbent material is provided underneath the digestible material in order to distribute digestor fluid across the surface of the digestible material.

11. A lid as claimed in claim 8 wherein a thin layer of absorbent material is provided underneath the digestible material in order to distribute digestor fluid across the surface of the digestible material.

12. A lid as claimed in claim 1 wherein the axial movement of the parts can be reversed.

13. A lid as claimed in claim 7 wherein the axial movement of the parts can be reversed.

14. A lid as claimed in claim 10 wherein the axial movement of the parts can be reversed.

15. A lid for closing a container comprising
a first part having an indentation adapted to receive a projection of a second part, the projection defining a cavity into which a spoilage monitoring device is received;
the spoilage monitoring device comprising a reservoir containing a digestor fluid and a tray containing a digestible material, wherein the tray has a base with a raised tactile pattern formed thereon and the digestible material is solid and covers the raised tactile surface, and the base of the tray defines a channel sealed by a valve that is opened on activation of the device; and wherein an axial movement of the parts relative to each other causes irreversible activation of the device such that the digestor fluid is absorbed by the digestible material liquefying it over a period of time, whereupon the digestible material is dissipated and a user is able to feel the raised tactile pattern.

* * * * *